(12) United States Patent
Walraevens et al.

(10) Patent No.: US 11,956,581 B2
(45) Date of Patent: Apr. 9, 2024

(54) MICROPHONE UNIT HAVING A PRESSURIZED CHAMBER

(71) Applicant: Cochlear Limited, Macquarie University (AU)

(72) Inventors: Joris Walraevens, Mechelen (BE); Patrik Kennes, Herent (BE); Vicente Osorio, Mechelen (BE); Stijn Eeckhoudt, Mechelen (BE); Koen Erik Van den Heuvel, Hove (BE)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 17/902,239

(22) Filed: Sep. 2, 2022

(65) Prior Publication Data
US 2023/0047075 A1 Feb. 16, 2023

Related U.S. Application Data

(63) Continuation of application No. 15/669,359, filed on Aug. 4, 2017, now Pat. No. 11,470,411.

(51) Int. Cl.
*A61N 1/36* (2006.01)
*A61N 1/05* (2006.01)
(Continued)

(52) U.S. Cl.
CPC ............ *H04R 1/08* (2013.01); *A61N 1/0541* (2013.01); *A61N 1/36038* (2017.08); *H04R 1/02* (2013.01); *H04R 1/222* (2013.01); *H04R 25/405* (2013.01); *H04R 25/604* (2013.01); *H04R 25/606* (2013.01); *H04R 31/003* (2013.01); *H04R 2201/003* (2013.01); *H04R 2225/41* (2013.01);
(Continued)

(58) Field of Classification Search
CPC .................. A61B 5/4836; A61B 5/686; A61B 2562/0219; A61B 2562/164; A61B 5/042; A61B 2562/0247; A61B 5/0031; A61B 5/486; A61B 5/7282; A61B 5/0051; H04R 2225/025; H04R 17/00; H04R 2225/67; H04R 25/604; H04R 3/00; A61N 1/05; A61N 1/36036; A61N 1/0541; A61N 1/36038
See application file for complete search history.

(56) References Cited

U.S. PATENT DOCUMENTS 5,802,198 A  9/1998 Beavers et al.
6,736,771 B2  5/2004 Sokolich et al.
(Continued)

OTHER PUBLICATIONS

International Search Report and Written Opinion for Application No. PCT/US2018/001011, dated Jan. 2, 2019.

*Primary Examiner* — Deborah L Malamud
(74) *Attorney, Agent, or Firm* — Edell, Shapiro & Finnan, LLC

(57) ABSTRACT

Disclosed examples generally include methods and apparatuses related to microphone units, such as may be found in implantable medical devices (e.g., cochlear implants). Microphone units generally include a microphone element connected to a chamber having a concave floor with the chamber covered by a membrane. Microphone units can be configured to produce an output based on pressure waves (e.g., sound waves) that reach the membrane. In an example, a microphone unit has a pressurized gas within the chamber below the membrane such that, while in a static state, the membrane deflects away from the chamber floor.

11 Claims, 8 Drawing Sheets

(51) Int. Cl.
  *H04R 1/02*   (2006.01)
  *H04R 1/08*   (2006.01)
  H04R 1/22    (2006.01)
  H04R 25/00   (2006.01)
  H04R 31/00   (2006.01)

(52) U.S. Cl.
  CPC ...... *H04R 2225/67* (2013.01); *H04R 2410/05* (2013.01)

(56) References Cited

U.S. PATENT DOCUMENTS

| | | |
|---|---|---|
| 7,204,799 B2 | 4/2007 | Miller, III et al. |
| 8,317,701 B2 | 11/2012 | Livne et al. |
| 8,509,469 B2 | 8/2013 | Miller, III et al. |
| 9,066,189 B2 | 6/2015 | Finberger |
| 9,533,143 B2 | 1/2017 | Van den Heuvel |
| 2003/0125602 A1 | 7/2003 | Sokolich |
| 2005/0101832 A1 | 5/2005 | Miller, III et al. |
| 2011/0200222 A1 | 8/2011 | Miller, III et al. |
| 2016/0295328 A1 | 10/2016 | Park |

MICROPHONE UNIT HAVING A PRESSURIZED CHAMBER

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate their auditory nerve in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Microphone units are disclosed. In one example, a microphone unit includes: a floor; a diaphragm spanning, and having a portion spaced apart from, the floor to define, at least in part, a chamber; and a pressure sensitive element in communication with the chamber, the pressure sensitive element configured to generate an output signal based on a pressure fluctuation in the chamber. The chamber is pressurized to deflect at least a portion of the diaphragm away from the floor.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
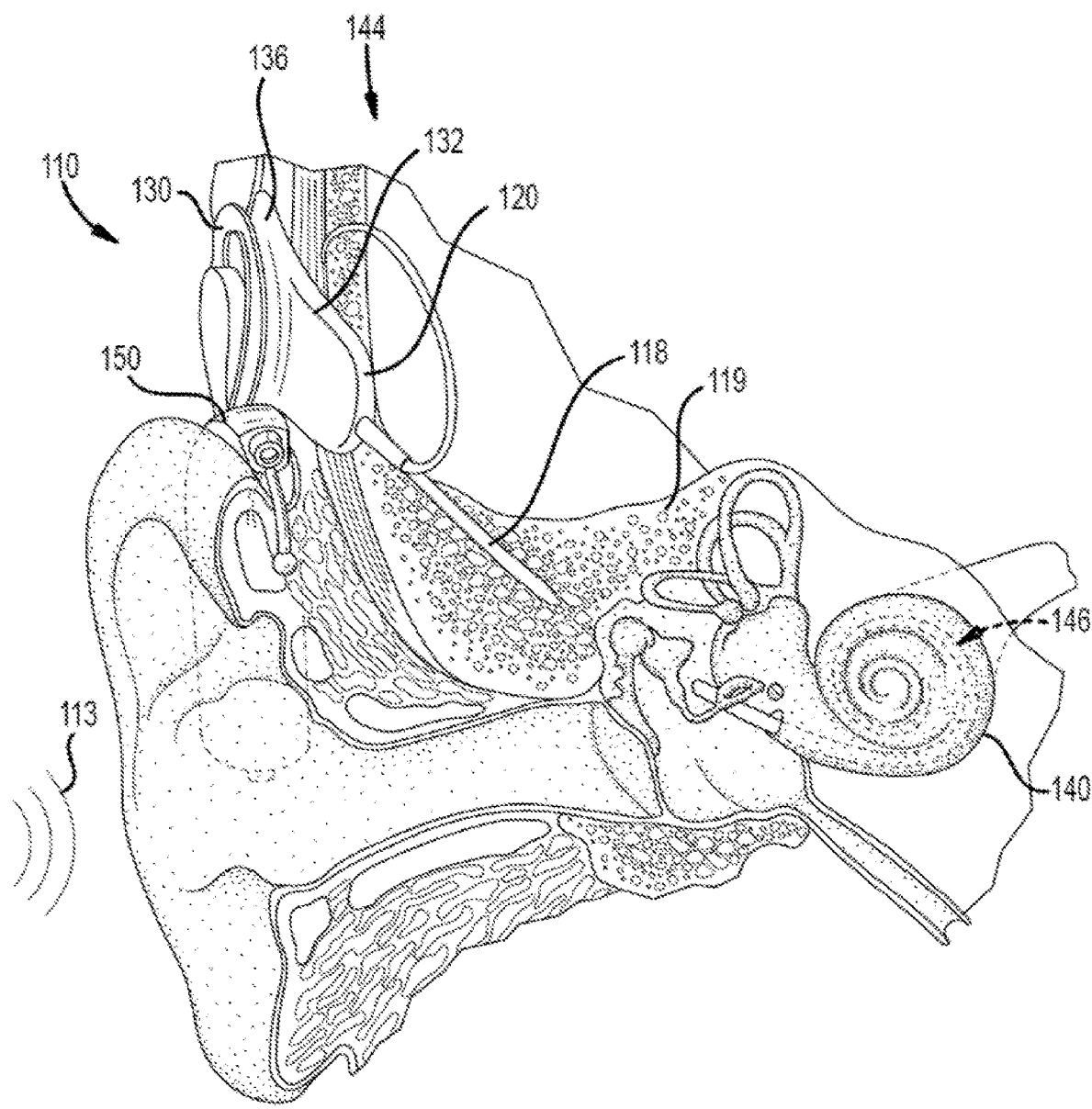
FIG. 1 illustrates an example cochlear implant system that includes an implantable component that can benefit from the use of a microphone unit in accordance with certain examples of the technology.

Disclosed examples include microphone unit technologies that can address one or more drawbacks of traditional microphone units, such as those found in conventional cochlear or middle-ear implants. Microphone units generally include a microphone element connected to a chamber defined by a concave floor and a flexible diaphragm or membrane spanning the floor to define the chamber. When pressure waves (e.g., sound waves) reach the membrane, the membrane can deflect in response to a pressure differential across the membrane. The amount of deflection is measured and an output indicative of the measurement is produced. In an example, a pressure change within the chamber is measured. The motion of the membrane causes pressure changes within the chamber, which are detected by the microphone element. The microphone element then converts the pressure changes into a usable form (e.g., for recording purposes, for controlling stimulation, etc.).

The technologies described herein can typically be used with medical devices, such as auditory prostheses (e.g., cochlear implants or middle-ear implants) and can also be used in other contexts. In an example, the microphone units disclosed herein can be applied in the context of a subcutaneous microphone. Traditional subcutaneous microphone units have drawbacks associated with performance of the membrane. In an example, membranes may have a tendency to deflect inward or outward depending on a curvature, manufacturing tolerances, ambient pressure, and other factors which can affect membrane performance. Further, unwanted inward deflection of the membrane can have a negative influence on acoustic sensitivity and other performance of the microphone. In addition, when a membrane bends inward, it can potentially touch the bottom of the chamber, which can impair proper functioning of the microphone, or even damage the membrane itself. Further, microphone units may require that the chamber include a concave floor to prevent the membrane from contacting the floor of the chamber. This chamber shape may be difficult to manufacture and may affect the sensitivity of the microphone unit.

There exists a need in the art for improvements to microphone units while avoiding some of the drawbacks of traditional techniques of microphone manufacture.

In an example, a microphone unit disclosed herein has a chamber filled with pressurized gas such that at least a portion of the membrane deflects away from the chamber floor while in a static state (e.g., where there is no substantial movement of the membrane). In this manner, the pressure between the membrane and the chamber floor causes the membrane to be biased away from the chamber floor and to be less sensitive to part or process variation, as well as to external pressure changes. The pressure within the chamber can further stiffen the membrane and increase the sensitivity, resonance peak, and bandwidth of the microphone. Additionally, the stiffened membrane can have higher resistance to being bent inward and potentially touching the bottom or floor of the chamber.

Deflection of the membrane due to pressure depends not only on the pressure within the chamber but also the pressure of the environment outside of the chamber. Where the pressure inside the chamber is greater than the pressure in the environment outside of the chamber beyond the membrane, the pressure within the chamber causes the membrane to deform away from the chamber floor and towards the lower-pressure environment. The pressure within the chamber can be selected such that the pressure within the chamber is greater than the pressure outside of the chamber during typical use conditions of the microphone unit. For example, the pressure of the environment can vary depending on the location of the microphone unit. The pressure of the environment outside the chamber depends, in part, on the location in which the microphone unit is located. For example, a microphone unit located at Denver, Colorado (approximately 5280 feet above sea level) will have a lower environmental pressure than a microphone unit located in Sydney, Australia (approximately 100 feet above sea level), which itself will have a lower environmental pressure the microphone located in Badwater Basin in Death Valley (approximately 275 feet below sea level). A sufficient pressure within the chamber is generally a pressure greater than one standard atmosphere (atm) of pressure, which corresponds to about 101.325 kilopascals of pressure. In some examples, the pressure is greater than about 1.1 atm, about 1.2 atm, about 1.3 atm, about 1.4 atm, about 1.5 atm, about 1.6 atm, about 1.7 atm, about 1.8 atm, about 1.9 atm, about 2.0 atm, about 2.5 atm, or about 3 atm. In other examples, the pressure can be even higher.

In an example, a sufficiently-pressurized chamber is a chamber with a pressure that deflects the membrane away from a chamber floor during use of a microphone unit at 1 atm. In another example, a sufficiently-pressurized chamber can have a pressure that prevents the membrane from contacting the floor of the chamber in a way that negatively affects performance of the microphone during typical use of the microphone unit (e.g., during use conditions recommended by the manufacturer of the microphone unit and not during contraindicated conditions). In yet another example, a sufficiently-pressurized chamber can be considered a chamber where the pressure-caused deflection of the membrane (e.g., as measured by the maximum distance between the membrane and the chamber floor) is on the range of tens of microns (e.g., approximately 20-100 microns) where there is an environmental pressure of 1 atm. In another example, a sufficiently-pressurized chamber can have a pressure-caused deflection of the membrane in the range of approximately 100-1000 microns measured where there is an environmental pressure of 1 atm.

Given that disclosed aspects can be applied to a wide variety of microphone units in a wide variety of contexts for use in a wide variety of environments, some experimentation can be used to determine suitable pressure and configuration of the microphone unit. Such experimentation can involve pressurizing a microphone unit, testing the performance of the microphone unit in an environment, and modifying the microphone unit or pressure in response to the results of the test. In an example, the size of membrane (e.g., its radius) can affect the behavior of the membrane. Generally, the larger the membrane, the lower the maximum pressure that is needed to achieve certain benefits of pressurization. Similarly, the elastic behavior of the membrane affects its behavior in response to pressurization. These and other characteristics can be modified to achieve desired results.

The disclosed microphone unit can be implemented in any of a variety of systems in accordance with examples of the technology. For example, in many examples, the microphone unit can be implemented within a conventional cochlear implant system. FIG. 1 depicts a conventional cochlear implant system that can benefit from the integration of the disclosed microphone unit components in accordance with certain examples of the technology.

FIG. 1 illustrates an example cochlear implant system 110 that includes an implantable component 144 typically having an internal receiver/transceiver unit 132, a stimulator unit 120, and an elongate lead 118. The implantable component 144 can further include a microphone unit (not shown) in accordance with many examples described herein.

The internal receiver/transceiver unit 132 permits the cochlear implant system 110 to receive signals from and/or transmit signals to an optional, external device 150. The external device 150, if any, can be a button sound processor worn on the head that includes a receiver/transceiver coil 130 and sound processing components. In other optional examples, the external device 150 can be just a receiver/transceiver coil in communication with a behind-the-ear device that includes the sound processing components and microphone. In still other examples, the external device 150 can provide power or control signals to the implantable component. The implantable component 144 includes an internal coil 136, and preferably, a magnet (not shown) fixed relative to the internal coil 136. The magnet is embedded in a pliable silicone or other biocompatible encapsulant, along with the internal coil 136. Signals sent generally correspond to external sound 113. The internal receiver/transceiver unit 132 and the stimulator unit 120 are hermetically sealed within a biocompatible housing, sometimes collectively referred to as a stimulator/receiver unit. The magnets facilitate the operational alignment of the external and internal coils, enabling the internal coil 136 to receive power and stimulation data from the external coil 130. The external coil 130 is contained within an external portion. The elongate lead 118 has a proximal end connected to the stimulator unit 120, and a distal end 146 implanted in a cochlea 140 of the recipient. The elongate lead 118 extends from stimulator unit 120 to the cochlea 140 through a mastoid bone 119 of the recipient.

In certain examples, the external coil 130 transmits electrical signals (e.g., power and stimulation data) to the internal coil 136 via a radio frequency (RF) link. The internal coil 136 is typically a wire antenna coil having of multiple turns of electrically insulated single-strand or multi-strand platinum or gold wire. The electrical insulation of the internal coil 136 can be provided by a flexible silicone molding. Various types of energy transfer, such as infrared (IR), electromagnetic, capacitive and inductive transfer, can be used to transfer the power and/or data from external device to cochlear implant.

As should be appreciated, while a particular cochlear implant that can benefit from utilizing the disclosed microphone unit has been illustrated and discussed above, the disclosed microphone unit can be integrated in any of a variety of different devices. Such devices need not necessarily be implantable and need not necessarily be medical devices. The above discussion is not meant to suggest that the disclosed microphone unit examples are only suitable for implementation within systems akin to that illustrated in and described with respect to FIG. 1. In general, additional configurations can be used to practice the methods and systems herein and/or some aspects described can be excluded without departing from the methods and systems disclosed herein. For example, in many examples microphone unit examples can be used with a totally-implantable cochlear implant as shown in FIG. 2.

Figure 2:
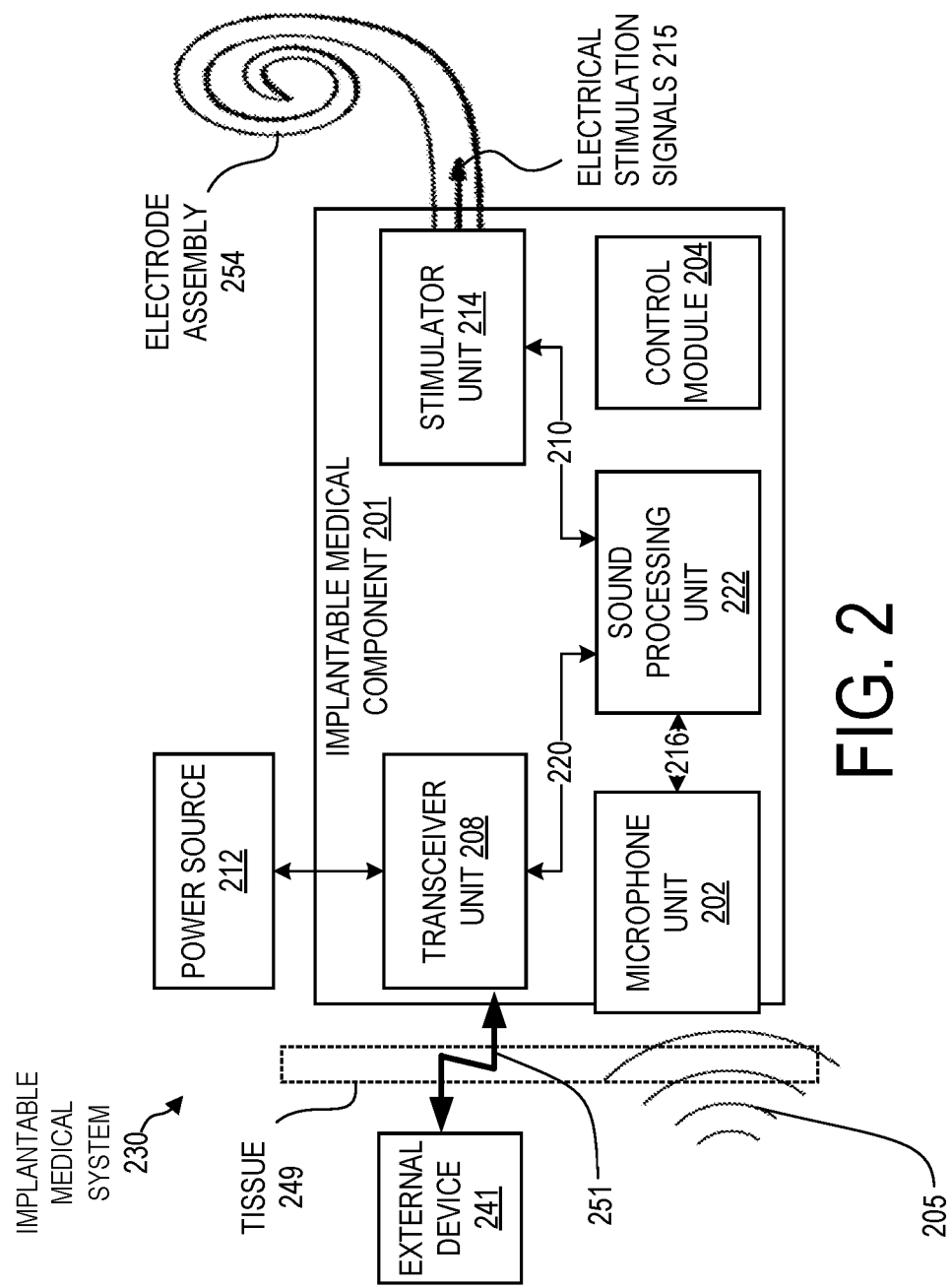
FIG. 2 is a functional block diagram of an example implantable medical device that can benefit from the use of a microphone unit in accordance with certain examples of the technology.

FIG. 2 is a functional block diagram illustrating an example implantable medical system 230 that is totally implantable, which can benefit from the inclusion of the microphone units described herein. The implantable medical system 230 can operate as for example, a cochlear implant. The depicted implantable medical system 230 is totally implantable insofar as all components of the implantable medical system 230 are configured to be implanted under skin or tissue 249 of the recipient. Because all components of the implantable medical system 230 are implantable, the implantable medical system 230 can operate, for at least a finite period of time, without the need of an external device. As such, an external device is optional. An external device 241 can be used to charge the internal battery, to supplement the performance of the implanted microphone/system, or for when the internal battery no longer functions. The external device 241 can be a dedicated charger or a conventional cochlear implant sound processor (e.g. a "behind-the-ear" sound processor or a "button sound processor").

The implantable medical system 230 includes a main implantable component 201 having a hermetically sealed, biocompatible housing. Disposed in the main implantable component 201 is a microphone unit 202 configured to sense a sound signal 205 and provide an output. The microphone unit 202 can be a microphone unit as described in relation to one or more microphone unit examples disclosed herein. Although shown in a unitary body as part of the implantable medical component 201, in an alternative, the microphone unit 202 and other aspects of the system can be included in an upgrade or tethered module outside of the main body of the implantable medical component 201.

An electrical signal 216 representing a sound signal 205 detected by microphone 202 is provided from the microphone 202 to the sound processing unit 222. The sound processing unit 222 implements one or more speech processing and/or coding strategies to convert the pre-processed microphone output into data signals 210 for use by the stimulator unit 214. The stimulator unit 214 uses data signals 210 to generate electrical stimulation signals 215 for delivery to the cochlea of the recipient. In the example of FIG. 2, the implantable medical system 230 includes an electrode assembly 254 for delivering stimulation signals 215 to the cochlea.

The main implantable component 201 further includes a control module 204. The control module 204 includes various components for controlling the operation of the implantable medical system 230, or for controlling specific components of the implantable medical system 230. For example, the control module 204 can control the delivery of power from a power storage element 212 of the implantable medical system 230 to other components of the system 230. For ease of illustration, the main implantable component 201 and the power storage element 212 are shown as separate. However, the power storage element 212 can alternatively be integrated into a hermetically sealed housing or part of a separate module coupled to the component 201. The hermetically sealed housing can be constructed from a biocompatible material, such as titanium.

The implantable medical system 230 further includes a receiver or transceiver unit 208 that permits the implantable medical system 230 to receive and/or transmit signals from/to an external device 241. For ease of illustration, the implantable medical system 230 is shown having the transceiver unit 208 in the main implantable component 201. In alternative arrangements, the implantable medical system 230 includes a receiver or transceiver unit which is implanted elsewhere in the recipient outside of the main implantable component 201.

As noted, the transceiver unit 208 can receive power and/or data from the external device 241. The external device 241 can include a power source (not shown) disposed in a Behind-The-Ear (BTE) unit. The external device 241 also includes components of a transcutaneous energy transfer link formed with the transceiver unit 208 to transfer the power and/or data to the cochlear implant system 230. The external device shown in FIG. 2 is merely illustrative, and other external devices can be alternatively used.

As should be appreciated, the various aspects (e.g., devices, components, etc.) described with respect to FIG. 2 are not intended to limit the systems and methods to the particular aspects described. Accordingly, additional configurations can be used to practice the methods and systems herein and/or some aspects described can be excluded without departing from the methods and systems disclosed herein. To be clear, the microphone units described below can be integrated in any of a variety of devices in accordance with examples of the technology.

Figure 3:
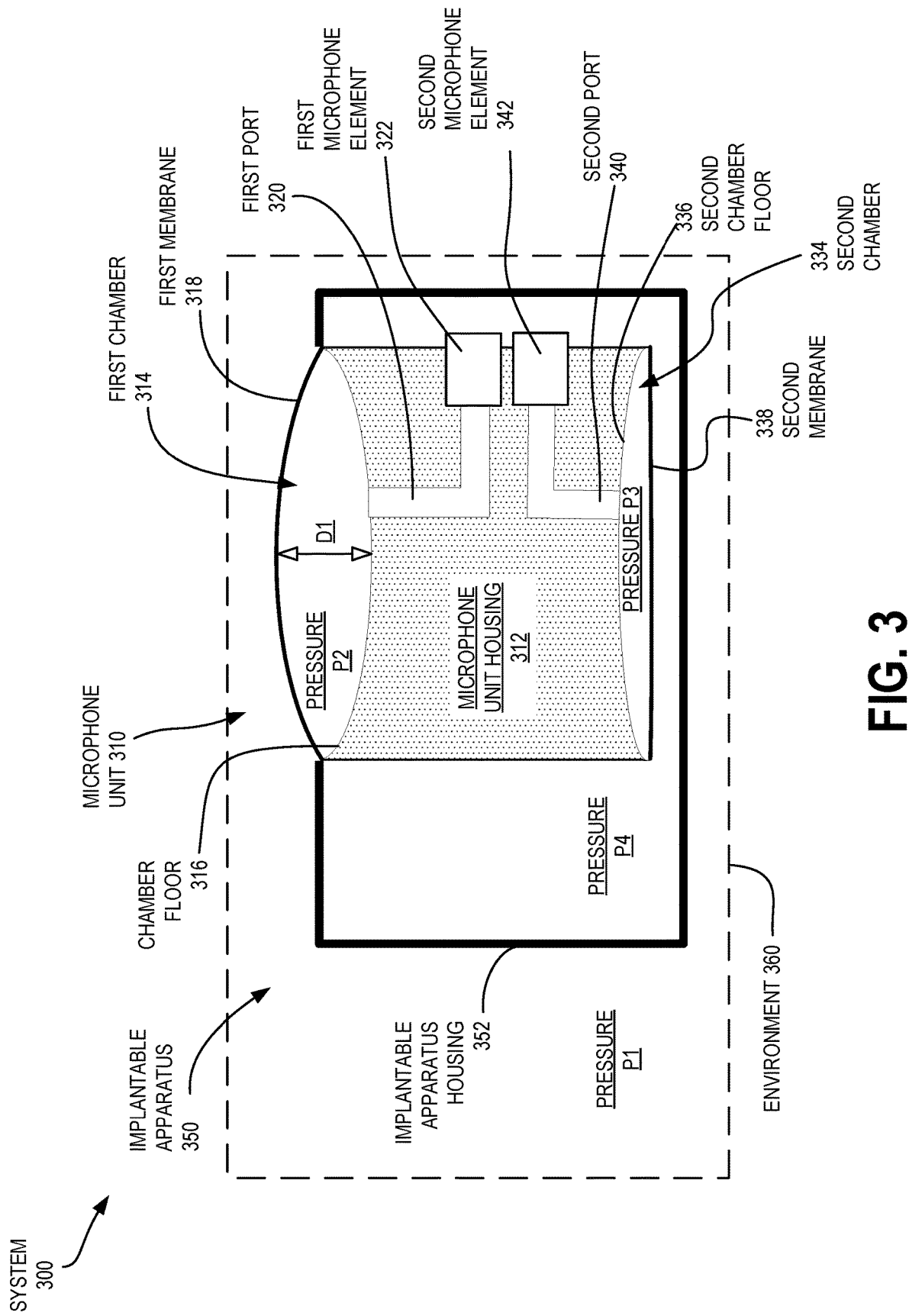
FIG. 3 illustrates an example system that includes a microphone unit that can be implemented with an implantable apparatus in accordance with certain examples of the technology.

FIG. 3 illustrates an example system 300 that includes a microphone unit 310 that can be implemented with an implantable apparatus 350 (e.g., a cochlear implant as described in relation to FIGS. 1 and 2) in accordance with certain examples of the technology. For example, as illustrated in the system 300, the microphone unit 310 is disposed within the implantable apparatus 350. The implantable apparatus 350 can be any one of a variety of different implantable medical devices or portions thereof, including but not limited to a totally implantable cochlear implant or a middle-ear implant. In some examples, the microphone unit 310 is integrated into a main body of a medical device (e.g., as illustrated by FIG. 2 which shows the microphone unit 202 disposed within the implantable medical component 201). In other examples, the microphone unit 310 is a standalone component attached to or otherwise connected to the medical device.

The microphone unit 310 includes a microphone unit housing 312 that houses components of the microphone unit 310. A volume of a first chamber 314 may be defined within the microphone unit housing 312. The first chamber 314 can be defined, at least in part, by a first chamber floor 316 and a first membrane 318 positioned across or spanning the first chamber floor 316 and forming a seal. In an example, the first membrane 318 has a thickness of approximately 25 microns and a diameter of approximately 11 mm, though other configurations may also be used. In some examples, the first chamber 314 may further be defined by chamber walls (not shown) or other arrangements in addition to the first chamber floor 316 and the first membrane 318. The first chamber 314 may be acoustically sealed, but need not necessarily be hermetically sealed, with respect to the microphone unit housing 312.

As illustrated, the microphone unit housing 312 further includes a first microphone element 322. The first microphone element 322 is a pressure-sensitive element configured to convert pressure changes measured within the first chamber 314 into a signal usable by another component (e.g., an electrical signal usable by a stimulator of the implantable apparatus 350). When a pressure wave reaches the first membrane 318, the first membrane 318 deflects toward the first chamber floor 316. This deflection causes a pressure change within the first chamber 314 that can be detected by the first microphone element 322. In some examples, the first microphone element 322 is placed directly in the first chamber floor 316. In other examples, the first microphone element 322 is connected to the first chamber 314 via a first port 320. The first port 320 can be a channel in the microphone unit 310 through which pressure changes can propagate.

The volumetric shape of the first chamber 314 can be defined—at least in part—by the first chamber floor 316 and first membrane 318. The shape can be modified in a variety of ways to increase the sensitivity of the microphone unit 310. Examples of such modifications are provided in U.S. Pat. No. 8,509,469 to Miller III, et al., which is incorporated herein by reference in its entirety for any and all purposes, including for its disclosure of chamber shapes and configurations. In an example, the first chamber 314 defines a conical or paraboloidal volume, such as by having a first chamber floor 316 with a conical or paraboloidal shape that is convex or concave.

The microphone unit 310 is disposed within the implantable apparatus 350. The implantable apparatus 350 includes an implantable apparatus housing 352. The microphone unit 310 may be disposed within the implantable apparatus housing 352 such that the first membrane 318 is not covered by the implantable apparatus housing 352. This allows the first membrane 318 to be exposed and responsive to incoming pressure waves (e.g., soundwaves).

The implantable apparatus 350 can be disposed within an environment 360. For example, where the implantable apparatus 350 is a totally implantable cochlear implant, the environment 360 may be a region beneath the recipient's skin. For example, a totally implantable cochlear implant may be positioned between a recipient's skull and skin. The microphone unit 310 can be positioned such that it can react to transcutaneous pressure waves received through the tissue of the environment 360. The first membrane 318 may therefore come into contact with tissue, so it can be beneficial for the membrane to be biocompatible (e.g., made from or coated in a biocompatible material). Similarly the implantable apparatus housing 352 can be biocompatible.

One challenge facing implantable microphones is their tendency to pick up body noises (e.g., vibrations originating from the circulatory, respiratory, skeletal, digestive, or other body systems). One technique for ameliorating the effect of these body noises, is to include a second microphone element. The second microphone element can be oriented to pick up body noises rather than externally-originating noises. The output of the second microphone element can then be combined with the output of the other microphone element in such a way to produce an output that better reflects external sound (e.g. without excessive influence from body noises). For example, a sound processing unit (e.g., sound processing unit 222 of FIG. 2) can take the output of both the first microphone element 322 and the second microphone element 342 and process them for improved quality.

Accordingly, in some examples, the implantable apparatus 350 can have a dual-microphone configuration to allow for improved microphone output quality (e.g., reducing the effect of body noises on the output). The second microphone can have its own microphone unit (not pictured) or be part of the same microphone unit 310. For example, the microphone unit housing 312 may further include a second chamber 334 defining a second chamber floor 336 and including a second membrane 338 sealing the second chamber 334. A second microphone element 342 may be connected to the second chamber 334 (e.g., connected via a second port 340). The orientation of the chambers 314 and 334 can be selected to improve output quality. For example, first chamber 314 may be oriented to face the skin of the patient (e.g., when the implantable apparatus 350 is a totally implantable cochlear implant), and the second chamber 334 may be oriented so it faces inward (e.g., towards a skull of the recipient). In this manner, the second membrane 338 may be less susceptible to pressure changes of the environment 360 than the first membrane 318. This can allow the output of the second microphone element 342 to more prominently include body noises than environmental noises compared to the first microphone element 322. Accordingly, the output of the first microphone element 322 and the output of the second microphone element 342 can be combined as part of a body-noise-reduction process to provide improved output. In some examples, the second microphone can be configured to act as an accelerometer.

As shown in FIG. 3, the environment 360 can have a pressure P1, the inside of the first chamber 314 can have a pressure P2, the second chamber 334 can have a pressure P3, and the pressure within the implantable apparatus 350 can have a pressure P4. As described herein, the microphone unit 310 can be configured to have and maintain a pressure P2 that is higher than the pressure P1 of the environment 360 during normal use. For example, the environment 360 will typically have a pressure P1 of approximately one standard atmosphere. The pressure P2 can be higher, such as 1.5 standard atmospheres of pressure. Because the pressure P2 within the first chamber 314 is higher than the pressure of the surrounding environment P1, the first membrane 318 will deflect away from the first chamber floor 316 and towards the environment 360. The deflection of the first membrane 318 can be measured by distance D1. Distance D1 is the furthest distance between the first membrane 318 and the first chamber floor 316 when the membrane is in a static state (e.g., not moving in response to a pressure wave). Depending on the configuration of the first chamber 314, the distance between the first membrane 318 and the first chamber floor 316 can vary. As previously discussed, the deflection can be in the range of tens or hundreds of microns, though other configurations are possible. In an example, the distance D1 is approximately 20 microns. In other examples, D1 is greater than 20 microns.

Increased pressure and deflection of the first membrane 318 can provide several advantages for the microphone unit 310, including advantages related to increased sensitivity and decreased likelihood of the first membrane 318 contacting the first chamber floor 316, among other advantages.

It is contemplated that while the pressure P2 of the first chamber 314 may be selected to be greater than the environmental pressure P1, there may nonetheless be circumstances where the pressure P1 is higher than the pressure P2. For example, the recipient of the implantable apparatus 350 may be underwater or within a hyperbaric chamber. In such circumstances, the environmental pressure may be higher than a typical pressure that the environment 360 may have when the user is simply going about day-to-day activities. Such increased pressure may cause the membrane to deflect inward because pressure P1 is greater than pressure P2.

The pressure of various regions within the implantable apparatus housing 352 may vary depending on the configuration of the apparatus 350 and the manner in which the apparatus 350 is manufactured. For example, depending on the configuration of the microphone unit 310, the pressure P3 of the second chamber 334 may, but need not, have a pressure the same as or substantially similar to pressure P2 of the first chamber 314. As described above, the second chamber 334 may, but need not, be pressurized. Depending on the configuration of the microphone unit housing 312 (and further, whether the first chamber 314 and the second chamber 334 are part of the same microphone unit housing 312), the pressure P3 and the pressure P2 may be substantially the same. For example, there may be small leaks from the chambers into the microphone unit housing 312 such that the pressures P2 and P3 equalize over time. In some examples, such leaks may be deliberately designed into the microphone unit housing or other components to allow for equalization of pressure between components. The leaks may also be caused by minor manufacturing defects, tolerances between components, or properties of the materials used.

Similarly, the pressure P4 within the housing 352 and outside the microphone unit 310 may, but need not be, the same as pressures P2 or P3. Again, there may be small leaks from the chambers into the microphone unit housing 312 such that the pressures P2, P3, and P4 equalize over time. In other examples, the microphone unit 310 may be sufficiently isolated from the rest of the implantable apparatus 350 such that the pressure P4 may be different from pressures P2 and P3.

While a specific microphone unit has been described above in association with FIG. 3, examples of the technology are not constrained to the specific aspects illustrated in FIG. 3. Microphone units can be implemented in any of a variety of ways in accordance with examples of the technology. For example, as already alluded to above, in many examples, implantable apparatuses do not include a second chambers and associated structures. Note also that the various regions can adopt any of a variety of geometries, and can be spatially oriented relative to one another in any of a variety of suitable ways in accordance with many examples of the technology.

Figure 4:
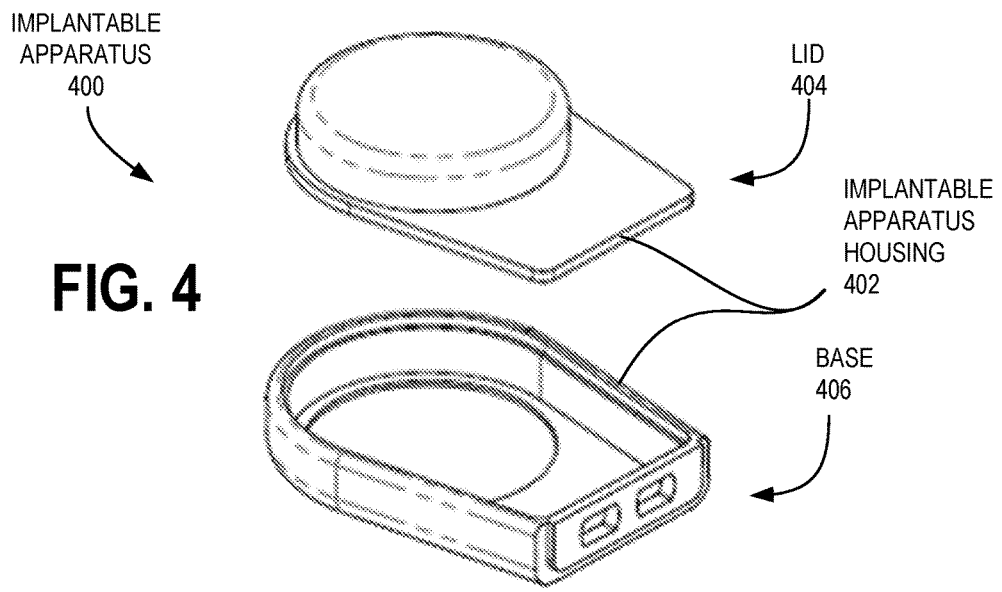
FIG. 4 illustrates an exploded view of an example configuration of an implantable apparatus in which aspects of a microphone unit can be used according to certain examples of the technology.

FIG. 4 illustrates an exploded view of an example configuration of an implantable apparatus 400 in which aspects of disclosed microphone units can be used according to certain aspects of the technology. In the illustrated example, the implantable apparatus housing 402 can include two primary portions: the lid 404 and the base 406. The lid 404 and the base 406 can be coupled together to form a seal to facilitate maintenance of a hermetic environment within the implantable apparatus 400. The seal may further facilitate maintenance of a pressurized environment within the implantable apparatus 400. As illustrated in FIG. 4, the housing 402 includes areas configured to receive, for example, feedthroughs and a membrane. Examples of the implantable apparatus 400 with these components installed is illustrated in FIGS. 5 and 6.

Figures 5, 6:
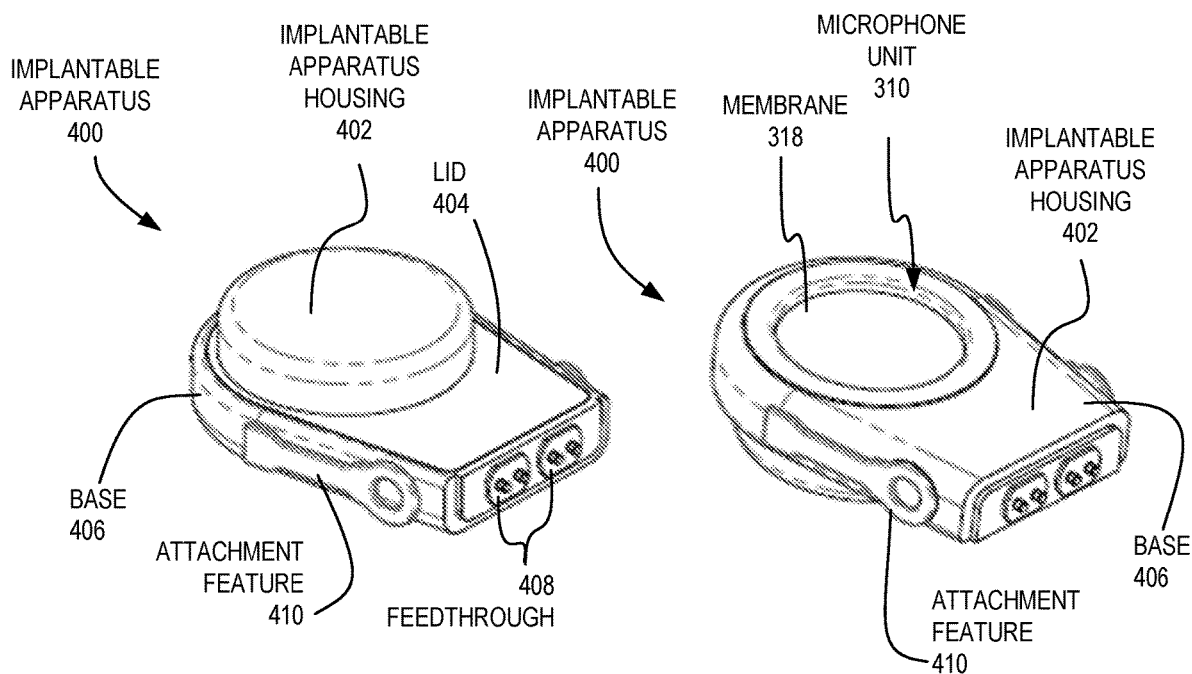
FIG. 5 illustrates a top perspective view of the implantable apparatus 400 with additional components installed in accordance with certain aspects of the technology.
FIG. 6 illustrates a bottom perspective view of the implantable apparatus 400 of FIG. 5 in accordance with certain aspects of the technology.

FIG. 5 illustrates a top perspective view of the implantable apparatus 400 with additional components installed in accordance with certain aspects of the technology. For example, as illustrated, the implantable apparatus further includes feedthroughs 408 for electrically coupling one or more portions of the implantable apparatus 400 to other components, such as a main body of an implantable device (e.g., in configurations where the implantable apparatus 400 is a standalone implantable microphone apparatus) or an electrode lead (e.g., lead 118 of FIG. 1) for delivering stimulation to a recipient. The implantable apparatus 400 further includes one or more attachment features 410. The attachment features 410 can facilitate connection between the implantable apparatus and the recipient. For example, the attachment features 410 can resist movement of the implantable apparatus 400 after implantation by connecting to the recipient's skull.

FIG. 6 illustrates a bottom perspective view of the implantable apparatus 400 of FIG. 5 in accordance with certain aspects of the technology. In this view, a first membrane 318 of a microphone unit 310 is visible. As previously discussed, the first membrane 318 can be on an outer portion of the implantable apparatus 400 to facilitate receiving pressure waves. The first membrane 318 can cooperate with the implantable apparatus housing 402 to form a hermetic seal for the implantable apparatus 400. Both the first membrane 318 and the implantable apparatus housing 402 can be made from or be coated in a biocompatible material.

Again, while a particular apparatus has been illustrated in and discussed with respect to FIGS. 4-6, it should be clear that a suitable apparatus can be implemented in any of a variety of ways in accordance with examples of the technology.

Figure 7:
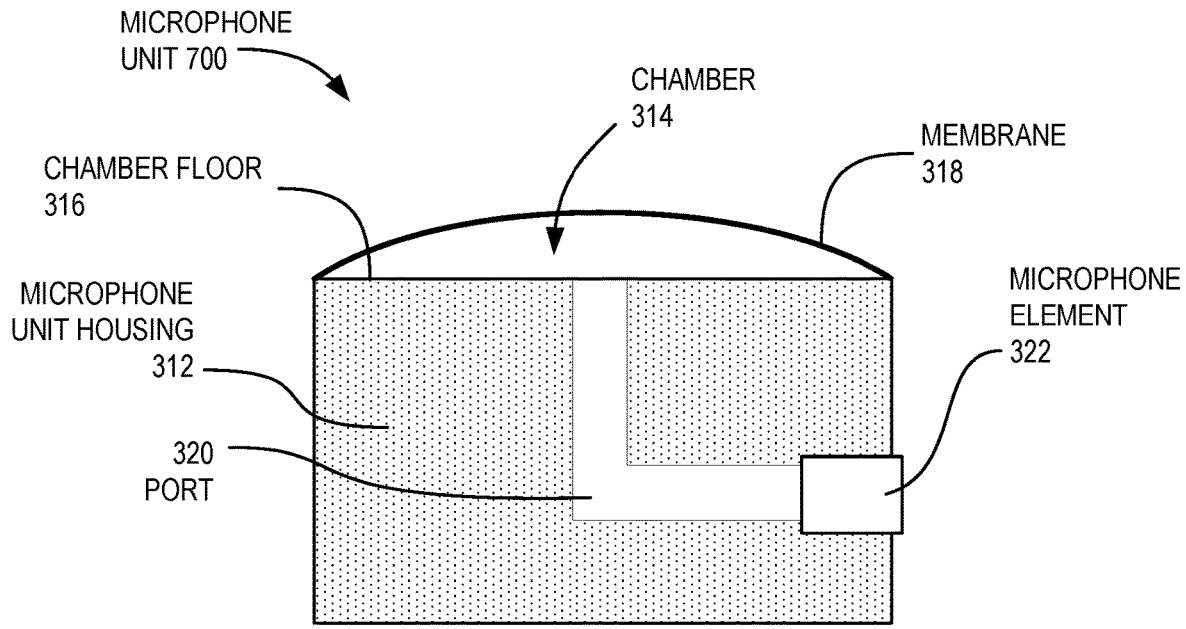
FIG. 7 illustrates an example microphone unit having a substantially flat chamber floor in accordance with certain aspects of the technology.
Figure 8:
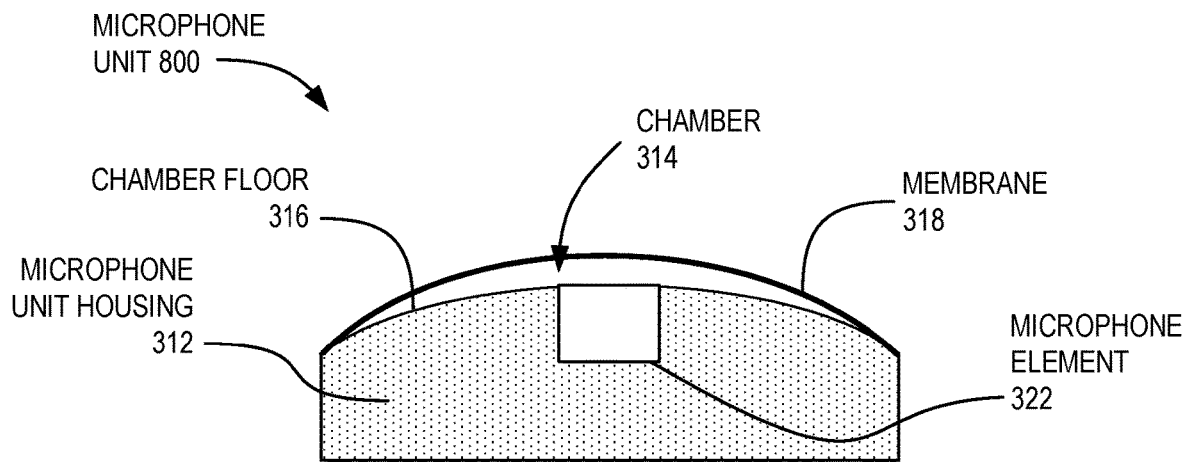
FIG. 8 illustrates a microphone unit where chamber floor has a convex shape in accordance with certain aspects of the technology.

FIGS. 7 and 8 illustrate example microphone units having non-concave chamber floors 316 in accordance with certain aspects of the technology. In traditional arrangements, a microphone's membrane is substantially flat and the chamber floor is concave to limit or resist the membrane contacting the chamber floor. Where the chamber is pressurized, however, the membrane deflects away from the chamber floor.

This deflection can allow the chamber floor to take on a variety of non-traditional shapes or configurations. Such non-traditional shapes can be selected to facilitate improved performance of the microphone unit and/or simplify otherwise complicated manufacturing. FIG. 7 illustrates an example microphone unit 700 having a substantially flat first chamber floor 316. FIG. 8 illustrates a microphone unit 800 where first chamber floor 316 has a convex shape that bows outward in the same direction as the first membrane 318. With this shape, the volume of the first chamber 314 is reduced, which can increase the sensitivity of the microphone unit 500. To be clear, examples of the technology can have a variety of different chamber configurations, including a variety of different chamber floor shapes and sizes.

Figure 9:
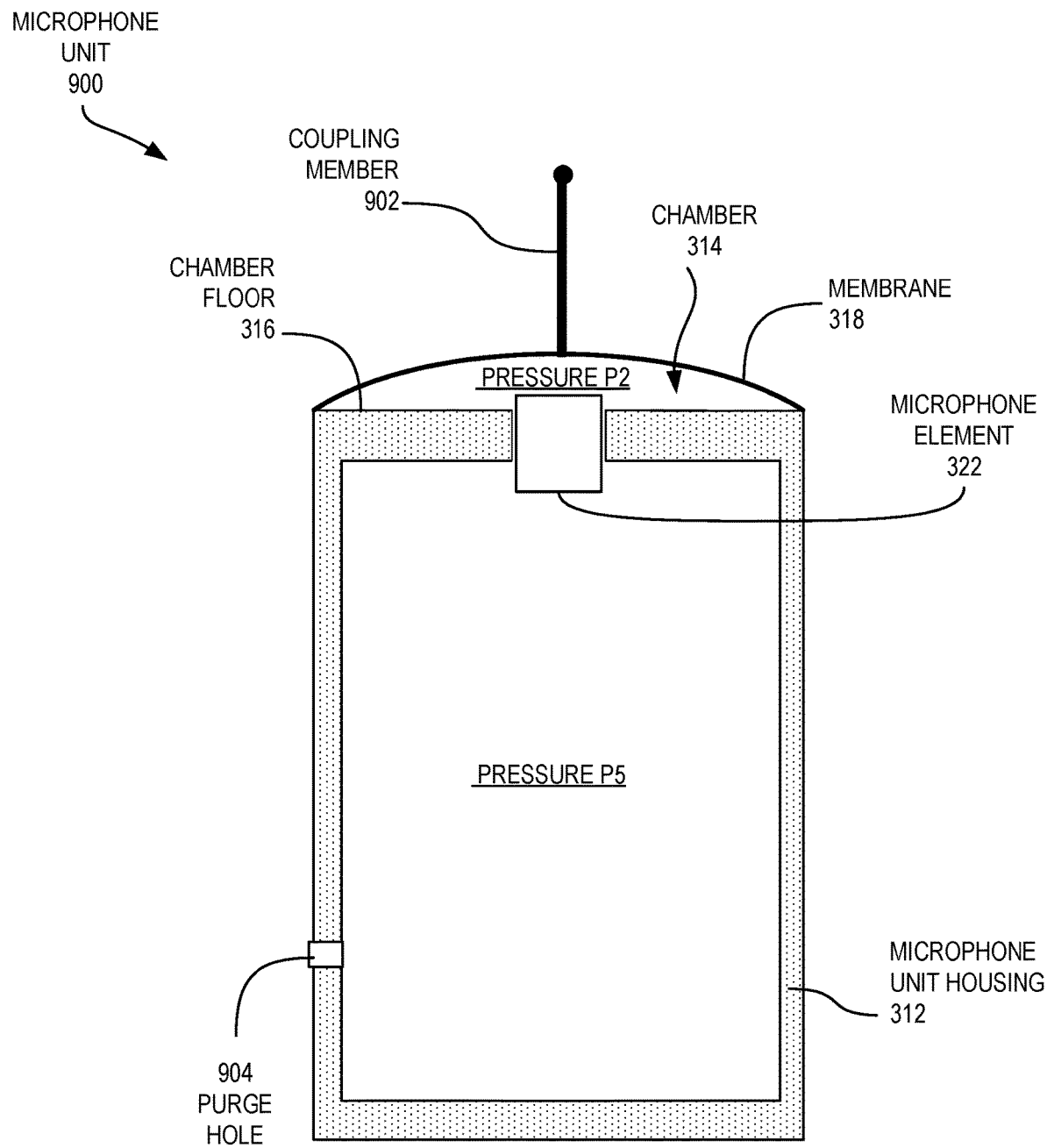
FIG. 9 illustrates a microphone unit configured with a coupling member for attaching the membrane to a vibrating structure of a recipient's ear in accordance with certain aspects of the technology.

As previously discussed, examples of the technology can be applied to a variety of different circumstances and apparatuses. While some previous examples generally contemplated membrane movement as a result of pressure waves propagating through overlying tissue (e.g., tissue 249 of FIG. 2), many disclosed examples can be applied in still other contexts. For example, the membrane can be coupled to a vibrating structure of a recipient's ear (e.g., the tympanic membrane or bones of the middle ear) such that vibrations of the vibrating structure are transferred to the membrane, causing the membrane to vibrate. Such a configuration can provide decreased sensitivity to internally-originating body noises. FIG. 9 illustrates an example microphone unit for use in such a configuration.

FIG. 9 illustrates a microphone unit 900 configured with a coupling member 902 for attaching the first membrane 318 to a vibrating structure of a recipient's ear such that the membrane vibrates responsive to vibration of the vibrating structure. An example of such a system is described in U.S. Pat. No. 9,533,143, which is incorporated herein by reference in its entirety for any and all purposes, including for its disclosure of a hearing device with a membrane that vibrates in response to vibration of a structure of the recipient's ear or fluid within one of the recipient's body cavities. In some examples, the coupling member 902 can be configured to couple to a structure of the recipient's middle or inner ear, and the coupling member 902 may include a rod or bracket suitable for coupling to the tympanic membrane. In other examples, the coupling member 902 can be configured to connect to the malleus, the incus, or the stapes, the elliptical window, round window, the horizontal canal, the posterior canal, or the superior canal. Via the connection with the coupling member 902, the coupling member 902 can influence the dynamics of the first membrane 318. As in other examples, the first chamber 314 can be pressurized to deflect the first membrane 318 away from the first chamber floor 316. This can further increase the sensitivity of the first microphone element 322 and provide improved performance. In an example, the first membrane 318 of the microphone unit 900 has a thickness of approximately 75 microns and a diameter of approximately 2-3 mm, though other configurations may be used to achieve desired results.

As illustrated, the microphone unit 900 further includes a purge hole 904. The purge hole 904 can be closed thereby sealing the microphone unit 900 to maintain the internal pressure P5 within the microphone unit 900, as well as the pressure P2 within the first chamber 314. This can facilitate creating and maintaining a particular pressure P2 (e.g., a pressure greater than one atmosphere). Sealing the purge hole 904 can facilitate maintenance of the pressure P5 within the microphone unit 900 and, more particularly, the pressure P2 within the first chamber 314. The pressure P2 within the first chamber 314 may, but need not, be distinct from the pressure P5 within the microphone unit 900 as a whole.

Figure 10:
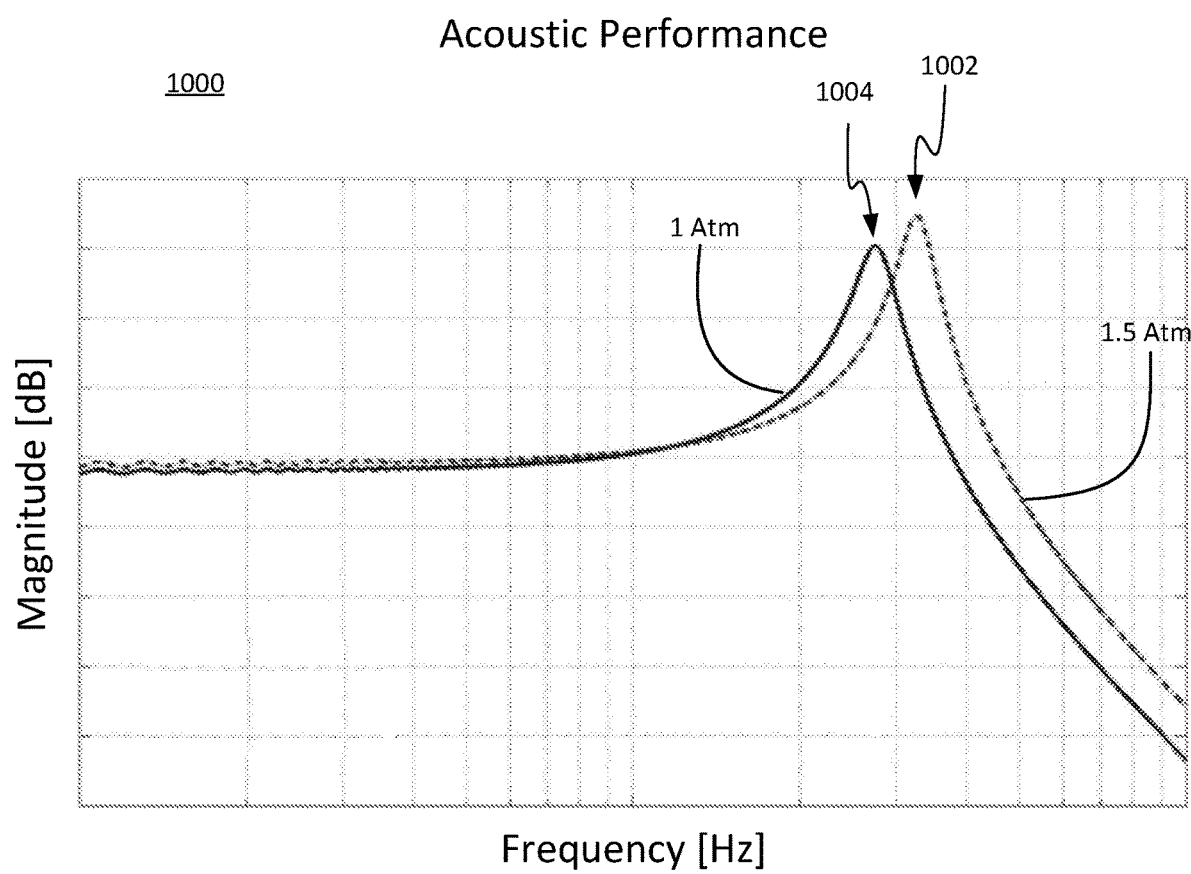
FIG. 10 illustrates a graph showing results of a simulation comparing acoustic performance of a chamber having a pressure of 1.5 atm compared to a chamber having a pressure of 1 atm in accordance with certain aspects of the technology

FIG. 10 illustrates a graph 1000 showing results of a simulation comparing acoustic performance of a chamber having a pressure of 1.5 atm compared to a chamber having a pressure of 1 atm. In particular, the graph 1000 compares frequency against decibel magnitude for the two different pressures: 1 atm and 1.5 atm. As shown, the response peak 1002 for the chamber having a higher pressure is shifted to higher frequencies compared to the response peak 1004 of the chamber having a lower pressure. This indicates that the frequency sensitivity of the chamber at a pressure of 1.5 atm is higher than the chamber having a pressure of 1 atm, indicating improved performance.

Figure 11:
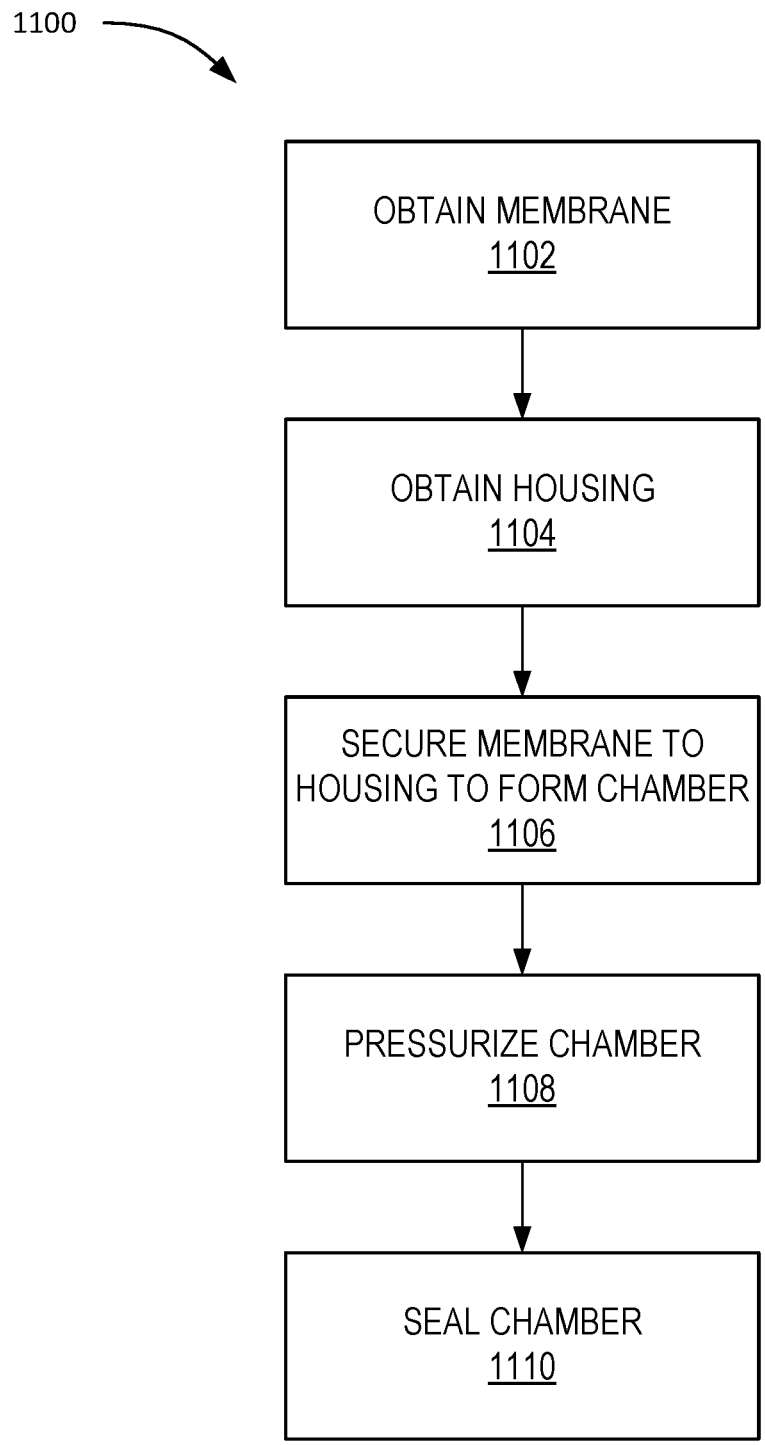
FIG. 11 illustrates an example process for manufacturing a microphone unit having a pressurized chamber in accordance with certain aspects of the technology.

FIG. 11 illustrates an example process 1100 for manufacturing a microphone unit having a pressurized chamber. The process 1100 can begin with operation 1102, which involves obtaining a membrane. This can include obtaining a suitable membrane for use with a microphone unit. The membrane may have a wide variety of shapes and sizes, and the membrane may be made from a variety of materials. The particular configuration of the membrane can vary depending on how it will be used, the device with which it will be used, and the environment in which it will be used.

At operation 1104, a housing is obtained. The housing can be an apparatus housing (e.g., apparatus housing 352 of FIG. 3), a microphone unit housing (e.g., microphone unit housing 312), or a combination thereof. In some examples, the membrane may be attached directly to the apparatus housing. In other examples, the membrane may be attached directly to the microphone unit housing, which in turn can be disposed within or coupled to the apparatus housing.

Again, the particulars of the housing can vary depending on a variety of factors, including applications in which the final product will be used. For example, where the device will be used within a recipient (e.g., wherein the device is a totally implantable cochlear implant), the housing can be biocompatible. The housing can have a variety of components already installed within it. For example, the housing can include components suitable for allowed the apparatus to function as or with a cochlear implant. The housing can include a microphone unit that defines a chamber floor, a microphone element, among other components.

At operation 1106, the membrane is secured to the housing to form a chamber. This can involve, applying the membrane over a portion of the housing that includes the chamber floor. Applying the membrane can include placing the membrane over the chamber floor such that the membrane is positioned away from the chamber floor when the chamber is pressurized. The membrane can be secured to the housing through any suitable technique given the housing and membrane materials. Such techniques can include but are not limited to welding and the use of adhesives. Depending on the configuration of the chamber, during this process, the membrane may be in contact with the floor of the chamber. For example, the chamber may have a substantially flat floor or a convex floor and rely on pressure in the chamber to deflect a least a portion of the membrane away from the floor. In such configurations, during manufacturing the membrane may be in contact with the floor and care may be taken in order to prevent damage to the membrane from contact with the floor. Later, after pressurization, the membrane may be deflect away from the floor of the chamber.

The chamber can be filled with a gas. In many examples, the gas will be air, but other gases can be used, such as an inert gas (e.g., nitrogen, helium, or argon). In still other examples, the chamber may be filled with a liquid. Where the chamber is filled with liquid, a suitable microphone element configured to operate in contact with liquid can be used. In other examples, the liquid can be contained in a separate volume or otherwise isolated from the microphone element.

At operation 1108, the chamber is pressurized. The chamber can be pressurized in a variety of ways. In a first example, the chamber is sealed (e.g., as described in operation 1110) while the chamber is within a pressurized manufacturing area (e.g., a pressurized welding station or other area). With the chamber sealed in the pressurized area, when the apparatus is moved to a non-pre-pressurized area, the seal chamber will remain pressurized relative to the surrounding environment. In another example, the chamber is filled with a gas at a pressure and then sealed. In yet another example, the chamber is filled with a cooled gas, such that when the gas warms to a particular temperature (e.g., room temperature, or body temperature), the chamber is at pressure.

At operation 1110, the chamber is sealed. The chamber can be sealed as part of the same process as securing the membrane to housing to form the chamber. In other examples, this can be a separate step involving, for example closing a purge hole or sealing another portion of the housing or device.

Although FIG. 11 illustrates the operations of the process 1100 as being in an order, they need not be. For example, one or more steps may occur concurrently or in a different order than is shown. In addition to the foregoing steps, additional steps can also be made.

This disclosure described some aspects of the present technology with reference to the accompanying drawings, in which only some of the possible aspects were shown.

Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A microphone unit configured to be implanted in a recipient, comprising:
    an implantable hermetically-sealed housing;
    a first chamber disposed in the implantable hermetically-sealed housing and comprising a first end and a second end;
    a second chamber disposed in the implantable hermetically-sealed housing and comprising a first end and a second end, wherein the first end of the second chamber is adjacent the second end of the first chamber;
    a first flexible membrane disposed across the first end of the first chamber;
    a microphone element disposed between the second end of the first chamber and the first end of the second chamber;
    a coupling member in communication with the first chamber and configured to generate an input signal based on vibration of a vibrating structure of the recipient, wherein the coupling member is disposed external to the implantable hermetically-sealed housing; and
    a pressurized fluid filling the first chamber and maintaining a first chamber pressure therein that is greater or less than an ambient pressure.

2. The microphone unit of claim 1, wherein in a static state of the microphone unit in which there is no substantial movement of the first flexible membrane, the first chamber pressure is sufficient to maintain the first flexible membrane deflected away from or inward toward the second end of the first chamber.

3. The microphone unit of claim 1, wherein in a static state of the microphone unit in which there is no substantial movement of the first flexible membrane, the first chamber pressure is greater than 1 standard atmosphere of pressure or less than 1 standard atmosphere of pressure.

4. The microphone unit of claim 1, further comprising a sealable purge hole.

5. The microphone unit of claim 4, wherein the sealable purge hole is fluidically coupled to the second chamber.

6. The microphone unit of claim 1, wherein the coupling member comprises an elongate element having a first end attached to the vibrating structure of the recipient and a second end attached to the first flexible membrane.

7. The microphone unit of claim 1, further comprising:
    an additional pressurized fluid filling the second chamber and maintaining a second chamber pressure within the second chamber.

8. The microphone unit of claim 7, wherein the second chamber pressure is the same as the first chamber pressure.

9. The microphone unit of claim 1, wherein the second end of the first chamber comprises a flat surface.

10. The microphone unit of claim 1, wherein the microphone element extends at least partially into the first chamber and the second chamber.

11. The microphone unit of claim 1, wherein the second end of the first chamber comprises an opening extending to the second chamber, and the microphone element is positioned within the opening.

* * * * *